United States Patent
Alexandre et al.

(10) Patent No.: US 6,837,866 B1
(45) Date of Patent: Jan. 4, 2005

(54) NEEDLELESS SYRINGE PROVIDED WITH AN EJECTION TUBE WITH A CONSTANT CROSS-SECTION

(75) Inventors: Patrick Alexandre, Gray (FR); Guy Delannoy, Saint Medard en Jalles (FR); Philippe Gautier, Le Plessis Pate (FR); Olivier Simonin, Toulouse (FR)

(73) Assignee: Crossject, Paris (FR)

( * ) Notice: Subject to any disclaimer, the term of this patent is extended or adjusted under 35 U.S.C. 154(b) by 108 days.

(21) Appl. No.: 10/129,562

(22) PCT Filed: Nov. 23, 2000

(86) PCT No.: PCT/FR00/03257

§ 371 (c)(1),
(2), (4) Date: May 6, 2002

(87) PCT Pub. No.: WO01/41840

PCT Pub. Date: Jun. 14, 2001

(30) Foreign Application Priority Data

Dec. 8, 1999 (FR) ............................. 99 15474

(51) Int. Cl.⁷ ................................ A61M 5/30
(52) U.S. Cl. ...................................... 604/69
(58) Field of Search ............................. 604/68, 69, 70, 604/131, 140, 141, 143

(56) References Cited

U.S. PATENT DOCUMENTS

| 4,124,024 A | * 11/1978 | Schwebel et al. ............. 604/69 |
| 5,204,253 A | 4/1993 | Sanford et al. |
| 5,630,796 A | * 5/1997 | Bellhouse et al. .......... 604/518 |
| 5,891,086 A | * 4/1999 | Weston ......................... 604/70 |
| 6,592,545 B1 | * 7/2003 | Bellhouse et al. ............. 604/69 |

FOREIGN PATENT DOCUMENTS

| WO | WO 94/24263 | 10/1994 |
| WO | WO 96/25190 | 8/1996 |
| WO | WO 01/05455 A1 | 1/2001 |

* cited by examiner

Primary Examiner—Brian L. Casler
Assistant Examiner—Kevin C Sirmons
(74) Attorney, Agent, or Firm—Oliff & Berridge, PLC

(57) ABSTRACT

The invention relates to a needless syringe (1), comprising in succession, a gas generator (2), a gas expansion chamber (3) and a means for retaining the particles of an active agent, comprising at least one lid (8) which breaks under the influence of the gas coming from the generator (2). The main characteristic of the inventive syringe (1) is that the tube (6) has a cylindrical upstream part in which the means retaining the particles are fixed, said upstream part having a substantially constant cross-section over a length that is more than twice its inner diameter.

19 Claims, 2 Drawing Sheets

NEEDLELESS SYRINGE PROVIDED WITH AN EJECTION TUBE WITH A CONSTANT CROSS-SECTION

The technical field of the invention is that of needleless syringes used for the subcutaneous or intramuscular injection of various active principles in pulverulent form for therapeutic use in human or veterinary medicine.

More specifically, the invention relates to a needleless syringe using a gas generator which is interded to create a pressure wave for ejecting the particles of active principle. A burstable protective seal, placed on the pathway of the gases, makes it possible to obtain the threshold pressure level permitting ejection of the particles at a sufficiently high speed. This is because the sudden release of the gases creates a thermodynamic shock in the syringe and it is the shock wave which will carry and accelerate the particles in order to expel them from the syringe. The specificity of the invention lies in the fact that the effect of the shock wave on the particles of active principle is improved by the specific geometry of the shock tube constituting the end part of the syringe through which said particles are expelled. Needleless syringes which function by release of a compressed gas in order to expel solid particles of active principle have already been the subject of several patents. Mention may be made, in particular, of patent application WO 94/24263 which describes a needleless syringe functioning by release of a reserve of gas in order to entrain the solid particles of active principle which are initially placed between two burstable transverse membranes, themselves positioned in the tube for ejection of the particles, said ejection tube having a convergent upstream part and a cylindrical downstream part which is straight or divergent. The characteristic of this syringe is that the two membranes are positioned in the convergent part of said tube, so that the portion of the tube situated downstream of the system for retention of the particles first has a convergent part which is then continued by a straight or divergent cylindrical part, the end of which is intented to come into contact with the skin of the patient who is to be treated.

Needleless syringes designed to inject solid particles of active principle must be fairly small but at the same time very efficient, the degree of efficiency being closely linked to the speed of expulsion of the particles, the minimum value of which speed is of the order of 750 m/s.

It remains a matter of particular interest to be able to improve the efficiency of a needleless syringe without having to increase its energy source or its dimensions. Thus, with this in mind, it has been observed that a syringe configuration in which, on the one hand, the free space, also called the expansion chamber and situated downstream of the energy source, has a cylindrical body continued by a zone of narrowing which opens into a cylindrical ejection tube of reduced cross section, and, on the other hand, the means for retention of the particles is situated at the inlet of said tube in continuity with said chamber, makes it possible to significantly increase the speed of the particles without having to modify the other characteristics of the syringe. This optimized configuration, with which a significant improvement in the efficiency of the syringe has been noted, differs from that described in patent WO 94 24263 in that the means for retention of the particles is situated in the ejection tube of constant cross section and not in the zone narrowing of the expansion chamber.

The needleless syringes according to the invention present this improvement.

The subject of the present invention is a needleless syringe comprising, in succession, a gas generator, a gas expansion chamber, a means for retention of the particles of an active principle, comprising at least one protective seal intended to burst under the effect of the gases coming from said generator, and a tube for ejection of said particles, characterized in that said tube has a cylindrical upstream part in which the means for retention of the particles is fixed, said upstream part having a substantially constant cross section along a length that is more than twice its internal diameter. The gas generator of the needleless syringe according to the invention can be a pyrotechnic gas generator involving a pyrotechnic charge and its initiating system, or can involve a reserve of compresses gas. In general, the gas generator can cover all possible forms as long as it causes an accumulation of gas in the expansion chamber sufficient to provoke rupture of the protective seal.

The gas expansion chamber is advantageously continued by said upstream part of the tube, and the protective seal, which is the most upstream element of the means for retention of the particles, constitutes, in a precise manner the limit between said chamber and said tube.

The protective seal is advantageously calibrated to yield at a dynamic pressure, in the chamber, of at least 70 bar, and preferably at a dynamic pressure of between 80 bar and 200 bar. The protective seal is advantageously prefragmented, so that it is intended to open out like petals under the effect of the thrust from the gases, without emitting particles.

The ejection tube is preferably a straight cylinder along its entire length.

According to a first preferred embodiment of the invention, the gas expansion chamber is substantially cylindrical and its internal diameter is close to that of the ejection tube. The diameters of the expansion chamber and of the ejection tube are preferably equal to 12 mm. The ratio of the sum of the lengths of the chamber and of the tube to their diameter is advantageously between 3 and 25, and preferably between 7 and 8.

According to a second preferred embodiment of the invention, the expansion chamber has a substantially cylindrical shape continued via a zone of narrowing which opens into the ejection tube, such that the internal diameter of said tube is smaller than the internal diameter of the cylindrical part of said chamber and the protective seal is fixed at the inlet of the ejection tube of reduced diameter.

The zone of narrowing is preferably progressive, having a convergent nozzle shape. In fact, the change from a configuration where the diameters of the chamber and of the tube are identical, to a configuration in which the diameter of the tube is smaller than that of the chamber, is always accompanied by an increase in the speeds of ejection of the particles of active principle, and this for one and the same energy source. It is also possible to imagine there being an abrupt zone of narrowing formed by an internal shoulder which mark a clear break between the chamber and the eject ion tube.

The ratio of the diameter of the cylindrical part of the expansion chamber to the internal diameter of the ejection tube is advantageously between 1.1 and 3, and preferably between 1.5 and 2.

The downstream segment of the tube, through which the particles are ejected, advantageously has a divergent conical part continued by a straight cylindrical part whose free end comes into contact with the skin. In this way, this divergent part makes it possible to increase the vent surface area and thus to decrease the pressure at the outlet of the syringe without significantly reducing the speed of ejection of the particles.

The straight cylindrical part continuing the divergent conical part of said tube preferably has a diameter identical to that of the cylindrical part of the chamber.

According to one or other of the two above preferred embodiments of the invention, the ratio of the length of the tube to the length of the chamber is between 1 and 5 and the sum of these two lengths is between 8 cm and 15 cm. The length of the chamber is preferably 3.5 cm and that of the tube 8.5 cm.

The diameter of the particles of active principle is advantageously between 20 μm and 100 μm, and preferably between 50 μm and 80 μm, and the total mass of said active principle is between 1 mg and 10 mg, and preferably between 2 mg and 7 mg. The particles are advantageously accomodated between the protective seal and a membrane placed downstream of said protective seal. Said membrane is preferably thin, nonelastic and transversal in relation to the axis of the tube and has lines of weakening in order also to open out like petals. The compaction of the particles is advantageously between 1% and 70%, and preferably between 10% and 50%. The compaction is defined as being the ratio of the total volume of the particles to the total volume of the ejection tube between the protective seal and the membrane.

The density of the particles of active principle is preferably between 1 and 18, and preferably between 3 and 10. Indeed, it is the combination of the two parameters of "diameter of the particles" and "density parameters of the particles" which will define their speed of ejection. In theory, the speed of the particles is inversely proportional to the density and to the square of the diameter. It has been demonstrated by means of calculation and tests that particles of small diameter can have high densities without thereby significantly affecting their speed. By contrast, if the particles are of a large size while at the same time having a high density too, the risk to be feared is that the shock wave issuing from the protective seal, which tears, will traverse these particles with high inertia and without actually entraining them along their complete course, the major consequence of which is a deceleration of the particles in relation to the entrainment gases and, ultimately, a speed of impact on the skin that is too slow to permit their penetration.

The cylindrical upstream part of the ejection tube advantageously has a substantially constant cross section along a length that is more than three and a half times its internal diameter.

The gas generator advantageously comprises a reserve of compressed gas which can be placed in communication with the gas expansion chamber. According to another embodiment of the invention, the gas generator is a pyrotechnic generator involving a pyrotechnic charge and a device for initiating said charge.

The needleless syringes according to the invention have the advantage that their level of efficiency is enhanced, in terms of speed of expulsion of the particles, without having to increase their energy source or their size.

Moreover, the particular geometry of the ejection tube of the needleless syringes according to the invention remains very simple and does not therefore necessitate sophisticated, time-consuming and expensive machining.

Finally, the needleless syringes according to the invention remain equally effective irrespective of whether they function with a pyrotechnic gas generator or use a generator involving a reserve of compressed gas.

Three preferred embodiments of the invention are described in detail below with reference to FIGS. 1 to 3.

Figure 1:
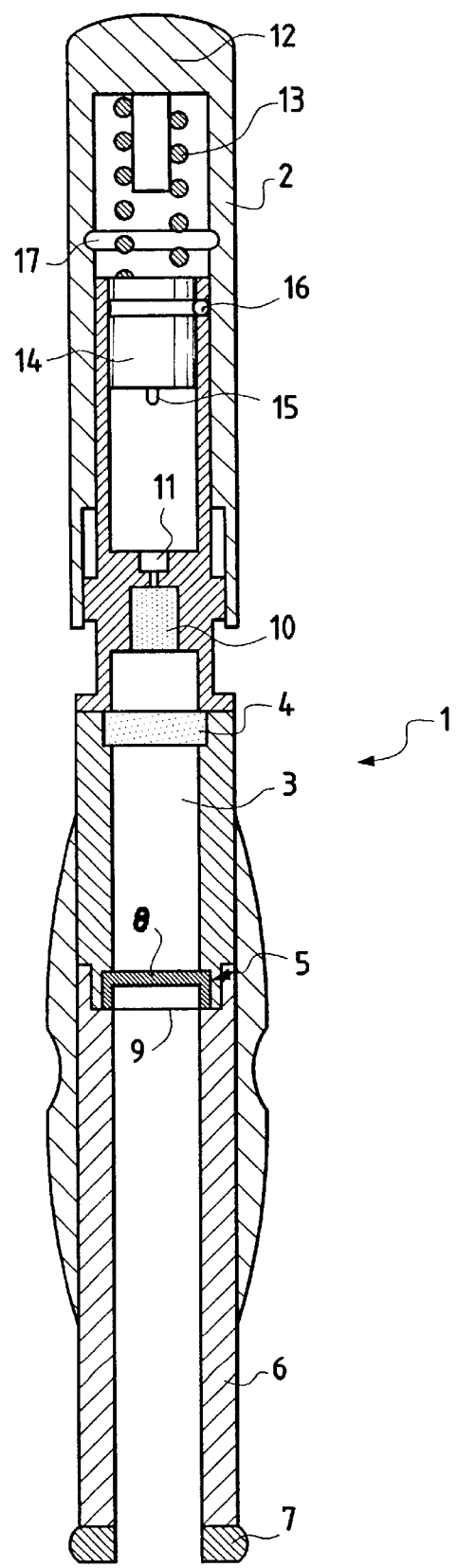
FIG. 1 is a longitudinal axial cross section through a needleless syringe according to the invention, in which the diameters of the expansion chamber and of the ejection tube are identical.
Figure 2:
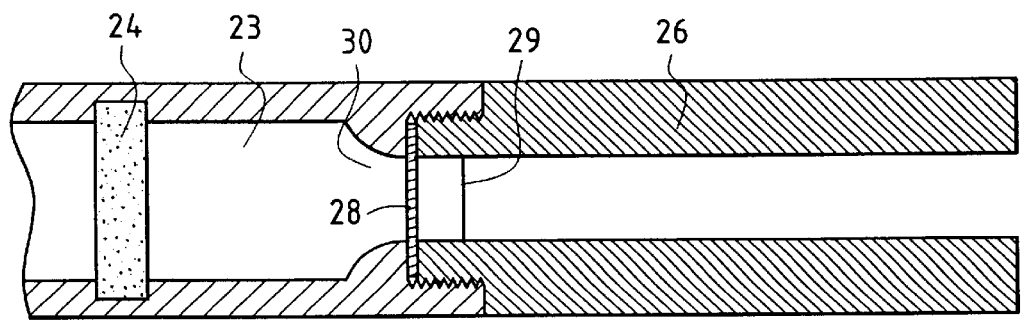
FIG. 2 is a diagram, in longitudinal axial cross section, of an expansion chamber having a zone of narrowing continued by a straight cylindrical ejection tube.

Referring to FIG. 1, a needleless syringe 1 according to the invention comprises, in succession, a pyrotechnic gas generator 2, an expansion chamber 3 equipped with a filter 4, a system 5 for retention of the particles, and the tube 6 used for ejection of said particles and intended to bear against the skin of the patient who is to be treated.

This bearing position can preferably be facilitated by means of a shock-absorbing rim 7 situated at the end of said tube 6. The gas expansion chamber 3 and the internal channel of the ejection tube 6 are of substantially cylindrical shape and both have the same diameter. The system 5 for retention of the particles, which marks the boundary between the chamber 3 and the tube 6, is made up of a burstable protective seal 8 and a thin membrane 9 placed downstream of said protective seal, these two elements being parallel to one another, in a position transverse with respect to the axis of the tube 6, and are both fixed to said tube 6. The particles of active principle occupy the space delimited by these two elements, with a degree of compaction preferably of between 1% and 70%.

According to a preferred embodiment of the invention, the length of the chamber 3 is 3.5 cm, the length of the ejection tube 6 is 8.5 cm, and their diameter is 0.8 cm. The burstable protective seal, which is situated on the side toward the expansion chamber 3, is calibrated in order to burst at a dynamic pressure at least equal to 70 bar, and the membrane 9 for its part serves exclusively to hold the particles in place, without presenting the slightest form of resistance to the gases which are produced.

Said membrane 9 is advantageously thin and nonelastic and, like the protective seal 8, it has lines of weakening defining a starshaped pattern so that it can open out like petals, without risking breaking open in orderly manner which could produce undesired fragments.

According to another embodiment, the membrane 9 can be replaced by a transverse grille which is likewise fixed to the inside of the tube 6 and contains, inserted within its interstices, the particles of active principle. In relation to the direction of propagation of the gases emitted, the protective seal 8 remains upstream of said grille.

At its end nearest to the pyrotechnic gas generator 2, the expansion chamber 3 has a transverse filter 4 which is intended, on the one hand, to trap certain solid particles generated by the combustion and, on the other hand, to cool the gases before they enter said chamber 3. Said filter 4 advantageously consists of a stack of metal grilles with an ever closer pitch and ending in a sheet of ceramic paper.

This filter 4 ensures that the temperature of the gases does not exceed 1500 K in the expansion chamber 3, so as not to damage the particles of active principle arranged in their seat. The pyrotechnic gas generator 2 comprises a device for initiating the pyrotechnic charge 10 and involving a percussion device and a primer 11. The percussion device, which is triggered by a push button 12, comprises a spring 13 and a weight 14 equipped with a striker 15. The weight 14 is blocked by at least one ball 16 wedged between said weight 14 and the push button 12, and said push button 12 has a circular inner groove 17.

Referring to FIG. 2, according to a second preferred embodiment of the invention, the needleless syringe comprises, in succession, a pyrotechnic gas generator (not shown in the figure), a gas expansion chamber 23, a means for retention of the particles, likewise consisting of a burstable protective seal 28 and a membrane 29 placed downstream of said protective seal, and a tube 26 for ejection of said particles. The chamber 23 has a filter 24 having the same functions as those described for the first preferred embodiment of the invention, namely trapping of the undesirable solid particles and cooling of the gases of combustion.

According to this preferred embodiment of the invention, the syringe has the same pyrotechnic gas generator as that described succinctly for the first preferred embodiment of the invention. The main difference from the first embodiment described hereinabove in the fact that the ejection tube 26 has a smaller internal diameter, smaller than that of the expansion chamber 23. More precisely, the expansion chamber 23 has a substantially cylindrical shape continued by a zone of progressive narrowing 30 which opens into the ejection tube 26, at the inlet of which the particles of active principle are accommodated, between the protective seal 28 and the membrane 29.

according to the second preferred embodiment of the invention, several configurations have been studied, in particular those in which the zone of narrowing is progressive in the shape of a convergent nozzle, and those in which the zone of narrowing is abrupt, formed by an internal shoulder. Table 1 below summarizes the configurations studied.

TABLE 1 configurations studied.

| CONFIGURATION | DESCRIPTION |
|---|---|
| Nominal | chamber diameter = 8 mm |
|  | tube diameter = 8 mm |
| Dcc 12 | chamber diameter = 12 mm |
|  | tube diameter = 8 mm |
| Dcc 16 | chamber diameter = 16 mm |
|  | tube diameter = 8 mm |
|  | zone of narrowing: abrupt |
| Cvg D12 | chamber diameter = 12 mm |
|  | tube diameter = 8 mm |
|  | zone of narrowing: progressive |
| Cvg D12-Opt | chamber diameter = 12 mm |
|  | tube diameter = 8 mm |
|  | zone of narrowing: progressive |
|  | optimized configuration |
| Cvg D16-Opt | chamber diameter = 16 mm |
|  | tube diameter = 8 mm |
|  | zone of narrowing: progressive |
|  | optimized configuration |

Dcc=abrupt zone of narrowing: an internal shoulder marks the limit between the chamber and the tube Cvg=progressive zone of narrowing in the shape of a convergent nozzle Opt=optimized configuration=configuration in which the sum of the length of the chamber and of the tube is equal to 10 cm Nominal=the chamber and the tube have the same diameter.

Graph 1 below gives the results obtained in terms of the speed of the gases and of the particles at the outlet of the tube, for each configuration studied.

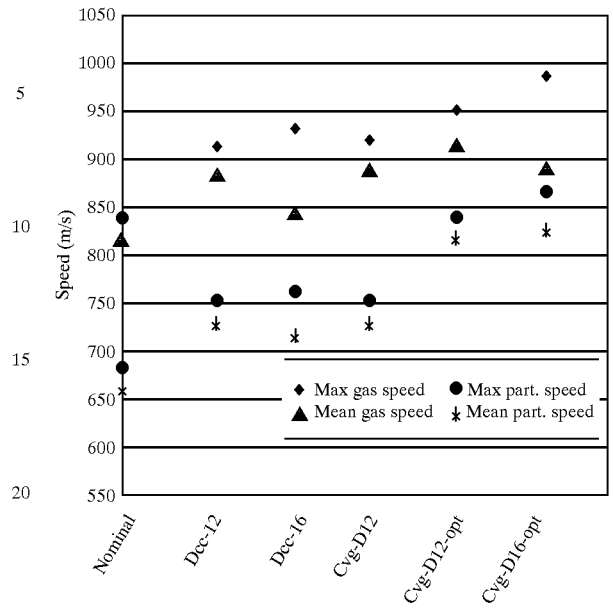

Graph 1 speed of the gases and of the particles at the outlet of the tube.

Table 2 below shows, for each configuration, the relative differences in mean speed of the particles between the configurations studied and the nominal configuration.

TABLE 2 gain in relative speed obtained for each configuration.

|  | $\Delta v/v$ |
|---|---|
| Nominal | 0 |
| Dcc 12 | +10.6% |
| Dcc 16 | +9.1% |
| Cvg D12 | +10.6% |
| Cvg D12-Opt | +23% |
| Cvg D16-Opt | +25% |

$\Delta v$=difference between the speed obtained with the configuration considered and that obtained with the nominal configuration v=nominal speed These results show clearly that, irrespective of the shape of the zone of narrowing of the expansion chamber, whether abrupt or progressive, there is a gain in the speed of the particles at the outlet of the ejection tube compared to the nominal configuration. Moreover, it is important to underline that this gain is a significant one, since it can attain a value of 25% in an optimized configuration.

The sum of the lengths of the chamber 23 and of the tube 26 is preferably 10 cm, and the diameters of the chamber 23 and of the tube 26 are 1.2 cm and 0.8 cm, respectively.

The zone of narrowing 30 preferably has the form of a convergent nozzle and its length is 0.6 cm. For a given pyrotechnic gas generator, the configuration in which the cross section of the tube 26 is smaller than that of the chamber 23 is more effective, in terms of speed of emission of particles of active principle, than that in which the chamber 3 and the tube 6 are in continuity with one another with the same diameter.

Figure 3:
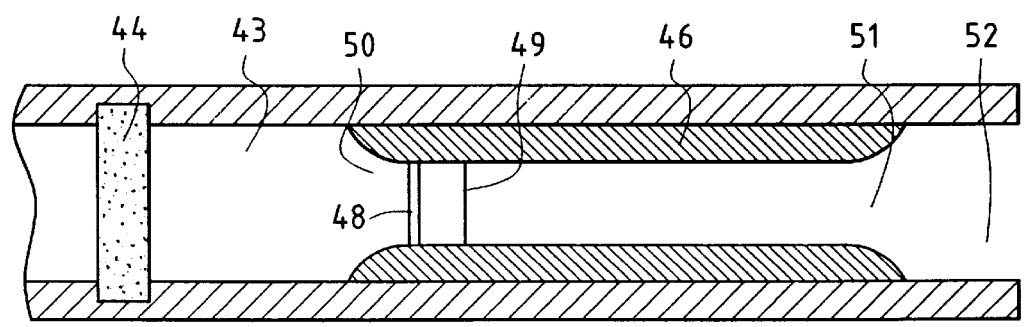
FIG. 3 is a diagram, in longitudinal axial cross section, of an expansion chamber similar to that in FIG. 2, in which the ejection tube has a divergent end part.

Referring to FIG. 3, according to a third preferred embodiment of the invention, the needleless syringe comprises, in succession, a pyrotechnic gas generator (not shown in the figure), a gas expansion chamber 43, a means for retention of the particles, likewise consisting of a burstable protective seal 48 and a membrane 49, and a tube 46 for ejection of said particles. The chamber 43 has a filter 44 which has the same functions as those described above. The ejection tube 46 has a reduced diameter smaller than that of the expansion chamber 43, said chamber 43 having a substantially cylindrical shape continued by a zone of progressive narrowing 50 which opens into the ejection tube 46. The system for retention of the particles is situated at the same location as that specified in the description of the second preferred embodiment of the invention. The fundamental difference compared with the second preferred embodiment of the invention is that the downstream segment of the tube 46 via which the particles are ejected has a divergent conical part 51 continued via a straight cylindrical part 52 whose free end comes into contact with the skin of the patient who is to be treated. This widening at the end constitutes a vent for the overpressure produced in the tube 46 and its main function is to disperse the residual pressure at the outlet of the syringe in such a way as to reduce any undesirable effect which could be harmful to the patient. This drop in pressure has practically no influence on the speed of the particles at the moment they impact the skin.

The dimensional characteristics of the second embodiment of the invention are retained for this third embodiment, and it should be added here that the length of the divergent conical zone 51 of the tube 46 is approximately 0.8 cm.

The straight cylindrical part 52 continuing the divergent conical part 51 of said tube 46 advantageously has a diameter identical to that of the cylindrical part of the chamber 43, said diameter being approximately 1.2 cm. Such a configuration, compared to the same configuration without divergent end part, allows the pressure to drop by 35% at the outlet of the tube 46.

What is claimed is:

1. A needleless syringe comprising, in succession, a gas generator (2), a gas expansion chamber (3, 23, 43), a means for retention of the particles of an active principle, comprising at least one protective seal intended to burst under the effect of the gases coming from said generator, and a tube (6, 26, 46) for ejection of said particles, characterized in that said tube (6, 26, 46) has a cylindrical upstream part in which the means for retention of the particles is fixed, said upstream part having a substantially constant cross section along a length that is more than twice its internal diameter.

2. The needleless syringe as claimed in claim 1, characterized in that the expansion chamber (3, 23, 43) is continued by said upstream part of the tube (6, 26, 46), and the protective seal (8, 28, 48), which is the most upstream element of the means for retention of the particles, constitutes the limit between said chamber (3, 23, 43) and said tube (6, 26, 46).

3. The needleless syringe as claimed in claim 2, characterized in that the protective seal (8, 28, 48) is calibrated to yield at a dynamic pressure, in the chamber (3, 23, 43), of at least 70 bar.

4. The needleless syringe as claimed in claim, 2, characterized in that the ejection tube (6) is a straight cylinder.

5. The needleless syringe as claimed in claim 4, characterized in that the gas expansion chamber (3) is substantially cylindrical and its internal diameter is close to that of the ejection tube (6).

6. The needleless syringe as claimed in claim 5, characterized in that the diameters of the (expansion chamber (3) and of the ejection tube (6) are equal to 12 mm.

7. The needleless syringe as claimed in claim 4, characterized in that the ratio of the sum of the lengths of the chamber (3) and of the tube (6) to their diameter is between 3 and 25.

8. The needleless syringe as claimed in claim 2, characterized in that the expansion chamber (23) has a substantially cylindrical shape continued via a zone of narrowing (30) which opens into the ejection tube (26), such that the internal diameter of said tube (26) is smaller than the internal diameter of the cylindrical part of said chamber (23) and the protective seal (28) is fixed in the ejection tube (26) of reduced diameter.

9. The needleless syringe as claimed in claim 8, characterized in that the zone of narrowing (30) is progressive, having a convergent nozzle shape.

10. The needleless syringe as claimed in claim 8, characterized in that the ratio of the diameter of the cylindrical part of the expansion chamber (23) to the internal diameter of the ejection tube (26) is between 1.1 and 3.

11. The needleless syringe as claimed in claim 8, characterized in that the ratio of the diameter of the cylindrical part of the expansion chamber (23) to the internal diameter of the ejection tube (26) is between 1.5 and 2.

12. The needleless syringe as claimed in claim 2, characterized in that the downstream segment of the tube (46), through which the particles are ejected, has a divergent conical part (51) continued by a straight cylindrical part (52) whose free end comes into contact with the skin.

13. The needleless syringe as claimed in claim 1, characterized in that the ratio of the length of the tube (6, 26, 46) to the length of the chamber (3, 23, 43) is between 1 and 5 and the sum of these two lengths is between 8 cm and 15 cm.

14. The needleless syringe as claimed in claim 1, characterized in that the diameter of the particles of active principle is between 20 $\mu$m and 100 $\mu$m, and the total mass of said active principle is between 1 mg and 10 mg.

15. The needleless syringe as claimed in claim 1, characterized in that the particles are accommodated between the protective seal (8, 28, 48) and a membrane (9, 29, 49) placed downstream of said protective seal (8, 28, 48).

16. The needleless syringe as claimed in claim 1, characterized in that the compaction of the particles is between 1% and 70%.

17. The needleless syringe as claimed in claim 1, characterized in that the density of the particles is between 1 and 18.

18. The needleless syringe as claimed in claim 1, characterized in that the cylindrical upstream part of the ejection tube (6, 26, 46) has a substantially constant cross section along a length that is more than three and a half times its internal diameter.

19. The needleless syringe as claimed in claim 1, characterized in that the gas generator comprises a reserve of compressed gas which can be placed in communication with the expansion chamber (3, 23, 43).

* * * * *